United States Patent
Pennington et al.

(10) Patent No.: US 6,335,446 B1
(45) Date of Patent: *Jan. 1, 2002

(54) QUINOLINIUM- AND PYRIDINIUM-BASED FLUORESCENT DYE COMPOUNDS

(75) Inventors: Mark William Pennington, Oxford; David Ian Scopes, Tubney; Michael Glen Orchard, Watlington, all of (GB)

(73) Assignee: Oxford Glycosciences (UK) Ltd., Abingdon (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/412,168

(22) Filed: Oct. 5, 1999

(30) Foreign Application Priority Data

| Oct. 5, 1998 | (GB) | ................................. 9821682 |
| Oct. 5, 1998 | (GB) | ................................. 9821683 |
| Oct. 5, 1998 | (GB) | ................................. 9821684 |

(51) Int. Cl.$^7$ .................. C07D 401/10; C07D 403/10; C07D 215/12; C07D 213/36; C07D 213/57
(52) U.S. Cl. .............. 544/359; 544/363; 544/124; 544/128; 546/172; 546/330; 546/334; 546/194; 546/276.4
(58) Field of Search ................... 544/359, 363, 544/124, 128; 546/330, 334, 172

(56) References Cited

U.S. PATENT DOCUMENTS 5,616,502 A * 4/1997 Haugland ..................... 436/86
5,912,257 A * 6/1999 Prasad ......................... 514/356

FOREIGN PATENT DOCUMENTS

| EP | 0 548 798 | 6/1993 |
| WO | WO 96/36882 | 11/1996 |
| WO | WO 98/23950 | 6/1998 |

OTHER PUBLICATIONS

Basili, 1997, "Development of a High–Throughput Fluorescence Scanner Employing Internal Reflection Optics and Phase–Sensitive Detection", Dissertation Abstracts 58(12–B):6686 (Ph.D. Thesis, University of Washington).

* cited by examiner

Primary Examiner—Evelyn Mei Huang
(74) Attorney, Agent, or Firm—Pennie & Edmonds LLP

(57) ABSTRACT

The present invention relates to quinolinium- and pyridinium-based fluorescent dyes. The dyes are useful for staining proteins in solution, in gels and on solid supports. The dyes of the invention exhibit higher fluorescence emission than known compounds when bound to proteins and also exhibit improved contrast of fluorescence intensity between their protein-bound and unbound states.

8 Claims, No Drawings

QUINOLINIUM- AND PYRIDINIUM-BASED FLUORESCENT DYE COMPOUNDS

1. FIELD OF THE INVENTION

The present invention relates to quinolinium- and pyridinium-based fluorescent dyes, and to their use in the staining of proteins in solution, in gels and on solid supports.

2. BACKGROUND OF THE INVENTION

Structures of formula II are disclosed in WO 96/36882, which discloses unsubstituted compounds (R1=R3=H) and the corresponding 2- and 2,6-substituted anilines, and those where the olefinic bond is optionally substituted (R4, R5=H, alkyl or phenyl), having fluorescence properties. A specific example of such a compound is shown in formula III.

Structures of formula IV are also disclosed in WO 96/36882, which discloses unsubstituted compounds (R1=R3=H) and the 2- and 2,6-substituted anilines, having fluorescence properties. A specific example of such a compound is shown in formula V.

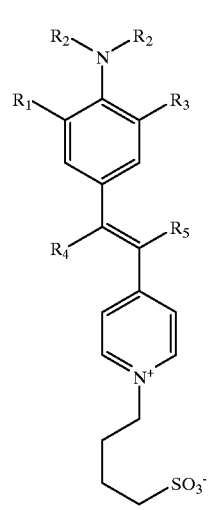

(II)

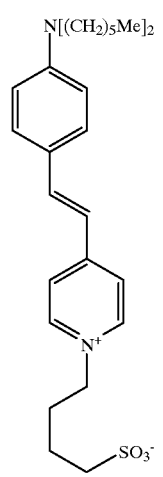

(III)

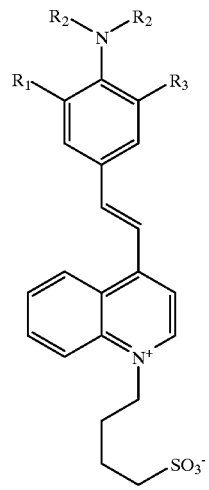

(IV)

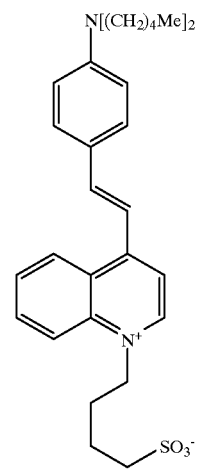

(V)

Citation of a reference herein shall not be construed as indicating that such reference is prior art to the present invention.

3. SUMMARY OF THE INVENTION

In a first aspect, the present invention relates to compounds of formula I

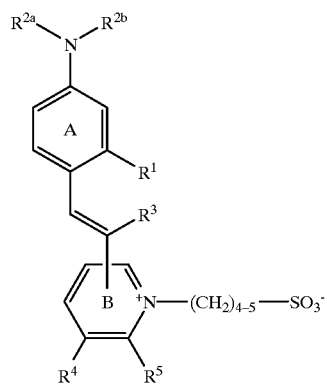

(I)

wherein $R^1$ is $(C_1-C_6)$ straight or branched chain alkyl, halogen or —$CF_3$;

either $R^{2a}$ and $R^{2b}$ are independently a lipophilic group or H, $R^{2a}$ and $R^{2b}$ not simultaneously being H, or $R^{2a}$ and $R^{2b}$ are taken together and form a morpholinyl, piperidinyl or pyrrolidinyl ring;

$R^3$ is H or $(C_1-C_6)$ straight or branched chain alkyl; and either $R^4$ and $R^5$ are both H, or $R^4$ and $R^5$ taken together are —CH=CH—CH=CH—, the aromatic rings A and B, the —$(CH_2)_{4-5}$— group, and the —C(H)=C($R^3$)— group being optionally substituted with one or more —OH, $(C_1-C_6)$ straight or branched chain alkoxyl, halogen, $(C_1-C_6)$ straight or branched chain haloalkyl, pyridyl, thiophenyl, furyl, and phenyl, the phenyl being optionally substituted with one or more —OH, $(C_1-C_6)$ straight or branched chain alkyl or $(C_1-C_6)$ straight or branched chain alkoxyl.

In a second aspect, the present invention relates to compounds of formula I wherein $R^1$ is H, $(C_1-C_6)$ straight or branched chain alkyl, halogen or —$CF_3$;

$R^{2a}$ and $R^{2b}$ are taken together to form —$(CH_2)_2$—$NR^6$—$(CH_2)_2$—, wherein $R^6$ is $(C_1-C_{12})$ straight or branched chain alkyl, $(C_1-C_{12})$ straight or branched chain alkylcarbonyl or $(C_1-C_{12})$ straight or branched chain alkylsulphonyl;

$R^3$ is H; and either $R^4$ and $R^5$ are both H, or $R^4$ and $R^5$ are taken together and form —CH=CH—CH=CH—, the aromatic rings A and B, the —$(CH_2)_{4-5}$— group, and the —C(H)=C($R^3$)— group being optionally substituted with one or more —OH, $(C_1-C_6)$ straight or branched chain alkoxyl, halogen, $(C_1-C_6)$ straight or branched chain haloalkyl, pyridyl, thiophenyl, furyl, and phenyl, the phenyl being optionally substituted with one or more —OH, $(C_1-C_6)$ straight or branched chain alkyl or $(C_1-C_6)$ straight or branched chain alkoxyl.

In a third aspect, the present invention relates to compounds of formula I wherein $R^1$ is H, $(C_1-C_6)$ straight or branched chain alkyl, halogen, or —$CF_3$;

either $R^{2a}$ and $R^{2b}$ are independently a lipophilic group or H, $R^{2a}$ and $R^{2b}$ not simultaneously being H, or $R^{2a}$ and $R^{2b}$ are taken together and form a morpholinyl, piperidinyl, pyrrolidinyl, or piperazinyl ring, wherein the piperazinyl ring is optionally substituted with $(C_1-C_{12})$ straight or branched chain alkyl, $(C_1-C_{12})$ straight or branched chain alkylcarbonyl or $(C_1-C_{12})$ straight or branched chain alkylsulphonyl;

$R^3$ is —CN, $CONH_2$, —COOH, or —COOR, wherein R is $(C_1-C_6)$ straight or branched chain alkyl or $(C_1-C_{10})$ straight or branched chain aralkyl, the —$CONH_2$ group being optionally substituted with one or two $(C_1-C_6)$ alkyl groups or one or two $(C_1-C_{10})$ aralkyl groups; and either $R^4$ and $R^5$ are both H, or $R^4$ and $R^5$ are taken together and form —CH=CH—CH=CH—, the aromatic rings A and B, the —$(CH_2)_{4-5}$— group, and the —C(H)=C($R^3$)— group being optionally substituted with one or more —OH, $(C_1-C_6)$ straight or branched chain alkoxyl, halogen, $(C_1-C_6)$ straight or branched chain haloalkyl, pyridyl, thiophenyl, furyl, and phenyl, the phenyl being optionally substituted with one or more —OH, $(C_1-C_6)$ straight or branched chain alkyl or $(C_1-C_6)$ straight or branched chain alkoxyl.

The present invention may be understood more fully by reference to the detailed description and illustrative examples which are intended to exemplify non-limiting embodiments of the invention.

4. DETAILED DESCRIPTION OF THE INVENTION

4.1 Definitions

As used herein, halogen refers to F, Cl, Br or I.

As used herein, $(C_1-C_6)$ straight or branched alkyl includes but is not limited to methyl, ethyl, n-propyl, propan-1-yl, propan-2-yl, cyclopropan-1-yl, n-butyl, butan-1-yl, butan-2-yl, 2-methyl-propan-1-yl, 2-methyl-propan-2-yl, cyclobutan-1-yl, 3-methyl-n-butyl, n-pentyl, pentan-1-yl, pentan-2-yl, cyclopentan-1-yl, n-hexyl, hexan-1-yl, hexan-2-yl, and cyclohexan-1-yl.

As used herein $(C_1-C_6)$ straight or branched chain alkoxy includes but is not limited to 2-hydroxyethyl, 2-hydroxypropyl, 3-hydroxypropyl, 4-hydroxybutyl, 1-hydroxybutyl, and 6-hydroxyhexyl.

As used herein, a lipophilic group refers to $(C_1-C_{20})$ straight or branched chain alkyl or $(C_1-C_{20})$ straight or branched chain aralkyl.

As used herein, $(C_1-C_{20})$ straight or branched chain alkyl includes but is not limited to methyl, ethyl, n-propyl, propan-1-yl, propan-2-yl, cyclopropan-1-yl, n-butyl, butan-1-yl, butan-2-yl, 2-methyl-propan-1-yl, 2-methyl-propan-2-yl, cyclobutan-1-yl, 3-methyl-n-butyl, n-pentyl, pentan-1-yl, pentan-2-yl, cyclopentan-1-yl, n-hexyl, hexan-1-yl, hexan-2-yl, and cyclohexan-1-yl, n-octyl, n-decyl, n-hexadecyl, n-octadecyl, and n-eicosyl.

As used herein, aryl refers to phenyl, naphthyl, or anthracenyl.

As used herein, $(C_1-C_6)$ straight or branched chain haloalkyl refers to an alkyl moiety, such as one of those listed above, having at least one halogen attached, including, but not limited to, —$CF_3$, —$CH_2F$, —$CHF_2$, —$CH_2I$, —$CH_2Br$, —$CH_2Cl$, —$CHCl_2$, —$CCl_3$, —$CH_2CHClCH_3$, —$CH_2C(CH_3)(CH_2Br)$, —$CH_2CH_2CH_2CH_2I$, —$C(CH_3)(CH_3)(CH_2F)$, and —$CH_2CHClCH_2CHClCH_2CH_3$. Preferably, the haloalkyl group is —$CF_3$.

As used herein, $(C_1-C_{12})$ straight or branched chain alkylcarbonyl refers to an alkyl moiety, such as those listed above, having one or more C=O groups attached.

As used herein, $(C_1-C_{12})$ straight or branched chain alkylsulphonyl refers to an alkyl moiety, such as those listed above, having one or more —$SO_2$— groups attached.

One skilled in the art will readily appreciate that when $R^4$ and $R^5$ taken together are —CH=CH—CH=CH—, aromatic ring B and —CH=CH—CH=CH— generate a quinoline system.

4.2 Compounds

The compounds of formula I have been found to display fluorescence properties superior to those of the prior art. Thus, in particular, certain compounds of the invention display much increased brightness over the compounds of formulae III and V when they are bound to protein (e.g. bovine serum albumin) and when sodium dodecyl sulphate is present in an amount below its critical micelle concentration. Furthermore, certain compounds of this invention display greater differences in the fluorescence intensities of their protein-bound and unbound states when compared to the compounds of formulae III and V.

Without being bound by any particular theory, Applicants believe that the compounds of formula I have properties superior to those described in WO 96/36882. In general terms, other substituents (both those shown in formula I, and also those not shown) may be less critical; thus, each of the aromatic rings, the —$(CH_2)_{4-5}$— group and the conjugating C═C link may carry other/further substituents that do not substantially affect the fluorescence intensity of the compounds (e.g. compounds have at least 50%, and preferably at least 75%, of the intensity of any compound illustrated herein under the same conditions). Examples of substituents are disclosed in WO 96/36882, the contents of which are incorporated herein by reference.

Preferred compounds of formula I, of the first aspect of the invention, include:

Quinolinium, 4-[2-[4-(dipentylamino)-32-chlorophenyl] ethenyl]-1(sulfobutyl)-, inner salt;

Quinolinium, 4-[2-[4-(dipentylamino)-32-trifluoromethylphenyl]ethenyl]-1-(sulfobutyl)-, inner salt;

Quinolinium, 4-[2-[4-(dipentylamino)-32-methylphenyl] ethenyl]-1-(sulfobutyl)-, inner salt;

Quinolinium, 4-[2-[4-(decylamino)-32-trifluoromethylphenyl]ethenyl]-1-(sulfobutyl)-, inner salt; and Pyridinium, 4-[2-[4-(dipentylamino)-32-trifluoromethylphenyl]ethenyl]-1-(sulfobutyl)-, inner salt.

Particularly preferred compounds of formula I, of the first aspect of the invention, are:

Quinolinium, 4-[2-[4-(dipentylamino)-3-trifluoromethylphenyl]ethenyl]-1-(sulfobutyl)-, inner salt;

Quinolinium, 4-[2-[4-(dipentylamino)-3-chlorophenyl] ethenyl]-1-(sulfobutyl)-, inner salt;

Quinolinium, 4-[2-[4-(decylamino)-3-trifluoromethylphenyl]ethenyl]-1-(sulfobutyl)-, inner salt; and Pyridinium, 4-[2-[4-(dipentylamino)-3-trifluoromethylphenyl]ethenyl]1 (sulfobutyl)-, inner salt.

Preferred compounds of formula I, of the second aspect of the invention, include:

Quinolinium, 4-[2-[4-[(1-oxooctyl)piperazinyl]phenyl] ethenyl]-1-(sulfobutyl)-, inner salt;

Quinolinium, 4-[2-[4-[(1-oxodecyl)piperazinyl]phenyl] ethenyl]-1-(sulfobutyl)-, inner salt;

Pyridinium,4-[2-[4-[(1-oxooctyl)piperazinyl]phenyl] ethenyl]-1-(sulfobutyl)-inner salt;

Pyridinium, 4-[2-[4-[(1-oxodecyl)piperazinyl]phenyl] ethenyl]-1(sulfobutyl)-, inner salt;

Pyridinium,2-[2-[4-[(1-oxooctyl)piperazinyl]phenyl] ethenyl]-1-(sulfobutyl)-inner salt; and Pyridinium, 2-[2-[4-[(1-oxodecyl)piperazinyl]phenyl] ethenyl]-1-(sulfobutyl)-, inner salt.

Preferred compounds of formula I, of the third aspect of the invention, include:

Pyridinium, 4-[2-[4-(dibutylamino)phenyl]-1-cyanoethenyl]-1-(sulfobutyl)-, inner salt; and Pyridinium, 4-[2-[4-(dihexylamino)phenyl]-1-cyanoethenyl]-1-(sulfobutyl)-, inner salt.

Compounds of formula I may be prepared from starting materials that are known by procedures known to those of ordinary skill in the art. By way of illustration, a synthesis of the compounds of formula I is shown in Scheme A, below. Compounds of formula Al are disclosed in EP-A-0548798. Non-limiting examples of the reactions involved may be found in, or based on, the Examples below. An illustrative synthesis of the compounds of formula I wherein $R^3$ is an electron withdrawing substituent as defined in the third aspect of the invention is shown in Scheme B, below.

Scheme A

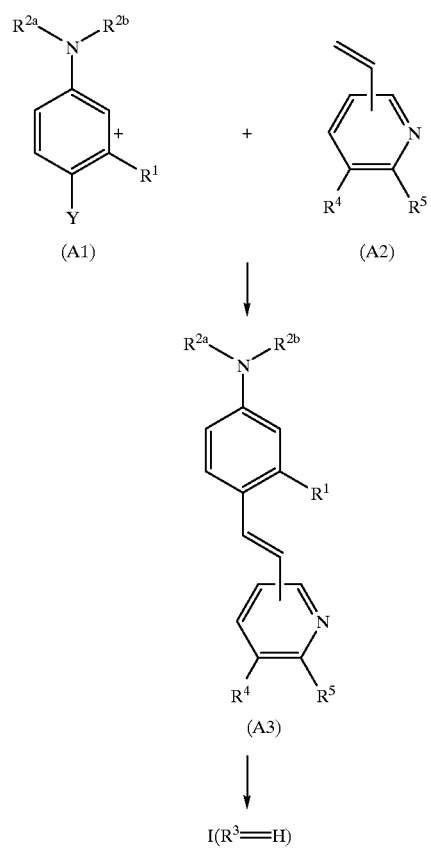

Scheme B

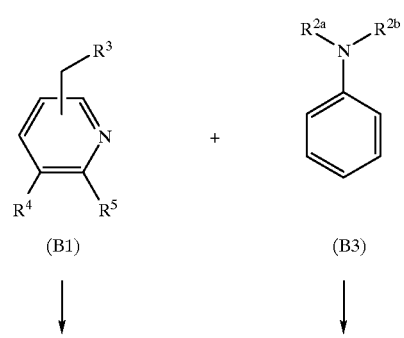

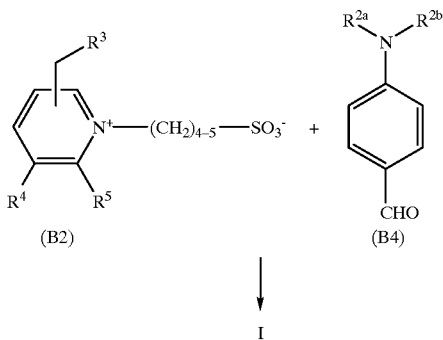

Compounds of the invention have utility in the visualisation of proteins following one-dimensional or 2-dimensional polyacrylamide gel electrophoresis ("PAGE").

Post-electrophoresis staining with such compounds allows the detection of proteins, typically down to the level of 2–20 femtomoles. Procedures for this purpose are known to those of ordinary skill in the art. A preferred system for 2-dimensional electrophoresis, detection, identification and isolation of proteins in biological samples is described in U.S. application Ser. No. 08/980,574, filed Dec. 1, 1997 (published as WO 98/23950), which is incorporated herein by reference in its entirety and which sets forth a preferred protocol at pages 29–35. In a preferred embodiment, a biological sample is treated, prior to electrophoresis, to enrich biomolecules (e.g. proteins) of interest or to deplete biomolecules (e.g. proteins) that are not of interest, as described in International Application No. PCT/GB99/01742, filed Jun. 1, 1999, which is incorporated by reference in its entirety, with particular reference to pages 3 and 6.

For example, a sample (e.g. plasma or serum) may be processed to deplete or remove one or more proteins such as albumin, haptoglobin, transferrin, alpha-1-antitrypsin, alpha-2-macroglobulin and immunoglobulin G (IgG) by performing affinity chromatography whereby the sample is passed through a series of columns containing immobilized antibodies for selective removal of albumin, haptoglobin, transferrin, alpha-1-antitrypsin and alpha-2-macroglobulin, and containing protein G for selective removal of IgG. In one such embodiment, two affinity columns in a tandem assembly are prepared by coupling antibodies to protein-G sepharose contained in 1 ml columns (Protein G-sepharose "Hi-Trap" columns, Pharmacia Cat. No. 17-0404-01) by circulating the following solutions sequentially through the columns: (1) Dulbecco's Phosphate Buffered Saline (Gibco BRL Cat. No.14190-094); (2) concentrated antibody solution; (3) 200 mM sodium carbonate buffer, pH 8.35; (4) cross-linking solution (200 mM sodium carbonate buffer, pH 8.35, 20 mM dimethylpimelimidate); and (5) 500 mM ethanolamine, 500 mM NaCl. A third (underivatized) protein G Hi-Trap column is then attached in series with and following the tandem antibody column assembly. The chromatographic procedure may be automated using an Akta Fast Protein Liquid Chromatography (FPLC) System such that a series of up to seven runs can be performed sequentially. The samples are passed through the series of 3 Hi-Trap columns, in which the affinity chromatography media selectively bind the above proteins, thereby depleting or removing them from the sample. Typically fractions (3 ml per tube) are collected of unbound material ("flowthrough fractions") that elutes through the column during column loading and washing, and of bound proteins ("bound/eluted fractions") that are eluted by step elution with Immunopure Gentle Ag/Ab Elution Buffer (Pierce Cat. No. 21013). The eluate containing unbound material is collected in fractions which are pooled, desalted and concentrated by centrifugal ultrafiltration, and stored to await further analysis.

A preferred scanner for detecting fluorescently labeled proteins is described in WO 96/36882 and in the Ph.D. thesis of David A. Basiji, entitled "Development of a High-throughput Fluorescence Scanner Employing Internal Reflection Optics and Phase-sensitive Detection (Total Internal Reflection, Electrophoresis)", University of Washington (1997), Volume 58/12-B of Dissertation Abstracts International, page 6686, the contents of each of which are incorporated herein by reference. This document describes a new image scanner designed specifically for automated, integrated operation at high speeds. The scanner can image gels that have been stained with fluorescent dyes or silver stains, as well as storage phosphor screens. The scanner incorporates a phase-sensitive detection system for discriminating modulated fluorescence from baseline noise due to laser scatter or homogeneous fluorescence. This capability increases the sensitivity of the instrument by an order of magnitude or more compared to conventional fluorescence imaging systems. The increased sensitivity reduces the sample-preparation load on the upstream instruments while the enhanced image quality simplifies image analysis downstream in the process.

5. EXAMPLES

The following illustrative examples are intended to be purely exemplary of the invention and are not intended to in any way limit its scope.

Example 1

Preparation of N,N-Dipentyl-4-bromo-3-chloroaniline (1).

1-Bromopentane (0.42 mL, 3.4 mmol) was added to a mixture of 4-bromo-3-chloroaniline (200 mg, 0.9 mmol) and potassium carbonate (199 mg, 1.4 mmol) in DMF (20 mL) and the reaction was heated to 13 0~~C overnight. The mixture was cooled, diluted with water (20 mL) and extracted with petroleum ether (3×25mL). The combined organic extracts were dried over sodium sulfate, filtered and concentrated under reduced pressure. The residue was purified via flash column chromatography using 9:1 petroleum ether:ethyl acetate as eluent to give N,N-Dipentyl-4-bromo-3-chloroaniline (1) (332 mg, 68%). $^1$HNMR (CDCl$_3$) 67.02 (d, lH, ArH); 3.12 (t, 4H, 2×NCH$_2$); 0.95 (t, 6H, 2×CH$_3$). MS; 347 (M+H).

Example 2

Preparation of N,N-Dipentyl-4-bromo-3-methylaniline (2).

Sodium triacetoxyborohydride (1.59 g, 7.5 mmol) was added to a solution of 4-bromo-3-methylaniline (265 mg, 1.4 mmol) and valeraldehyde (8.0 mL, 7.5 mmol) in methanol (25 mL). After stirring for 3 hours the reaction was quenched with aq. saturated sodium hydrogen carbonate solution (25 mL) and extracted with petroleum ether (3×25mL), The combined organic extracts were dried over sodium sulfate, filtered and concentrated under reduced pressure. The residue was purified via flash column chromatography using petroleum ether as eluent to give N,N-Dipentyl-4-bromo-3-methylaniline (2) (440 mg, 95%). $^1$HNMR (CDCl$_3$) 67.14 (d, 1H, ArH). 3.22 (t, 4H, 2×NCH$_2$); 0.82 (t, 6H, 2×CH$_3$). ThC (silica gel): Rf=0.30 (petroleum ether).

Example 3
Preparation of N,N-Dipentyl-4-bromo-3-trifluoromethylaniline (3).

Sodium hydride (480 mg, 1.5 eq.) was added to a solution of 4-bromo-3-trifluoromethylaniline (1.92 g, 5 mmol) and 1-bromopentane (3 mL, 3 eq.) in dimethylformamide (10 mL) at 0° C. After 1 hour a further (320 mg, 1 eq.) of sodium hydride was added and the reaction was left overnight. The reaction was heated to 50° C. and left overnight. The reaction was quenched with methanol and partitioned between water and petroleum ether. The organic extract was concentrated under reduced pressure and the residue was purified via flash column chromatography using petroleum ether as eluent to give N,N-Dipentyl-4-bromo-3-trifluoromethylaniline (3) (2.84 g. 93%). $^1$H NMIR (CDCl$_3$) δ 7.34 (d, 1H, ArH); 6.80 (d, 1H, ArH); 6.52 (dd, 1H, ArH); 3.18 (t, 4H, 2×NCH$_2$); 0.86 (t, 6H, CH~1b). TLC (silica gel): RI~0.55 (petroleum ether).

Example 4
Preparation of N-Decyl-4-bromo-3-trifluoromethylaniline (4).

Sodium triacetoxyborohydride (4 g) was added to a solution of 3-trifluoromethyl-4-bromoaniline (1.5 g) and decanal (4 mL) in methanol (90 mL). After stirring for 1 h the solution was partitioned between water and petroleum ether. The organic extract was concentrated under reduced pressure and the residue was purified via flash column chromatography using petroleum ether as eluent to give N-Decyl-4-broma-3-trifluoromethylaniline (4) (1.2 g, 53%). $^1$H NMR (CDCl$_3$) δ 7.44 (d, 1H, ArH); 6.92 (d, 1H, ArH); 6.61 (dd, 1H, ArH); 3.11 (t, 2H, NCH$_2$); 0.80 (t, 3H, CH$_2$CH$_3$). TLC (silica gel): Rf=0.35 (petroleum ether).

Example 5
Preparation of Intermediate (5)

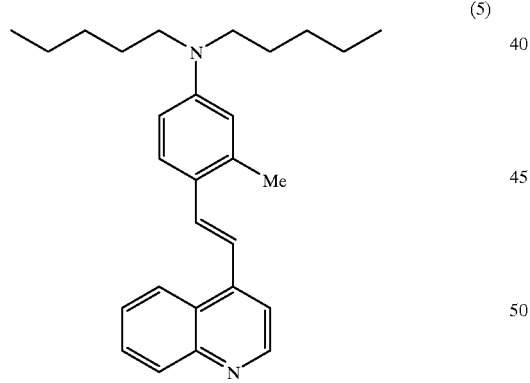

(5)

Palladium diacetate (2 mg, 0.008 mmol) and tri-o-tolylphosphine (24 mg, 0.08 mmol) were added to a solution of N,N-dipentyl-4-bromo-3-methylaniline (Intermediate 2) (250 mg, 0.77 mmol) and 4-vinylquinoline (108 mg, 0.70 mmol) in triethylamine (10 mL). The reaction mixture was heated at reflux for 48 hours. The reaction was cooled, diluted with water (10 mL) and extracted with dichloromethane (3×20 mL). The combined organic extracts were dried over sodium sulfate, filtered and concentrated under reduced pressure. The residue was subjected to flash column chromatography, using 8:2 petroleum ether:ethyl acetate as eluent, to give Intermediate (5) which was used directly in the next step.

Example 6
Preparation of Intermediate (6)

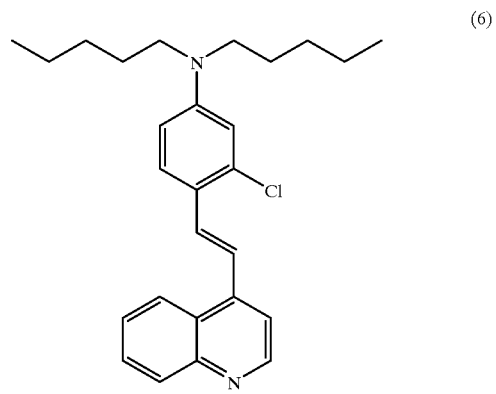

(6)

Palladium diacetate (9 mg, 0.04 mmol) and tri-o-tolylphosphine (24 mg, 0.04 mmol) were added to a solution of N,N-dipentyl-4-bromo-3-chloroaniline (Intermediate 1) (120 mg, 0.35 mmol) and 4-vinylquinoline (60 mg, 0.4 mmol) in triethylamine (10 mL). The reaction mixture was heated at reflux for 48 hours. The reaction was then cooled, diluted with water (10 mL) and extracted with dichloromethane (3×20 mL). The combined organic extracts were dried over sodium sulfate, filtered and concentrated under reduced pressure. The residue was subjected to flash column chromatography, using 8:2 petroleum ether:ethyl acetate as eluent, to give Intermediate (6) which was used directly in the next step.

Example 7
Preparation of Intermediate (7)

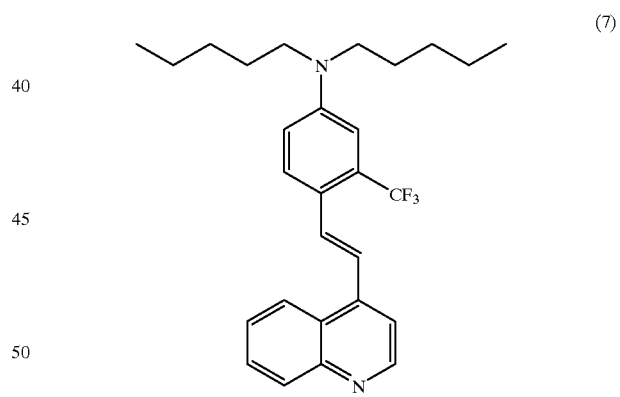

(7)

Palladium diacetate (30 mg, ca. 5 mol %) triphenylphosphine (35 mg, ca. 5 mol %) potassium acetate (745 mg, 1 eq.) and tetra-N-butylammonium chloride (ca. 0.8 g, 1 eq.) were added to a solution of N,N-dipentyl-4-bromo-3-trifluoromethylaniline (Intermediate 3) (760 mg) and 4-vinylquinoline (360 mg, 1.1 eq.) in dimethylformamide (5 mL). The reaction mixture was heated at 110° C. for 4 hours then further palladium diacetate (30 mg) and triphenylphosphine (35 mg) were added. After 6 h, tetra-N-butylammonium chloride (0.6 g) was added and the reaction left overnight. The reaction was then heated to 130° C. for 4 h, diluted with water (10 mL) and extracted with dichloromethane (3×5mL). The combined organic extracts were dried over sodium sulfate, filtered and concentrated under reduced pressure. The residue was purified via flash column chromatography, using a gradient of 0→16% ethyl acetate-:petroleum ether as eluent, to give Intermediate (7) (180 mg (20%). $^1$H NMR (CDCl$_3$) δ 8.72 (d, 1H, ArH); 6.75 (m, 1H, ArH); 6.54 (dd, 1H, ArH); 3.22 (t, 4H, 2×NCH$_2$); 0.78 (t, 6H, 2×CH$_2$CH$_3$). TLC (silica gel): Rf=0.7 (30% ethyl acetate:petroleum ether).

Example 8

Preparation of Intermediate (8)

Palladium diacetate (35 mg, ca. 5 mol %), triphenylphosphine (88 mg, ca. 10 mol %),

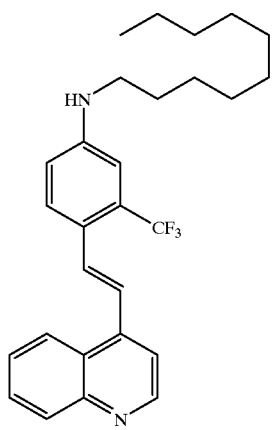

(8)

potassium acetate (ca. 1 g, 1 eq.) and tetra-N-butylammonium chloride (ca. 0.9 g, 1 eq.) were added to a solution of N-decyl-4-bromo-3-trifluoromethylaniline (Intermediate 4) (1.2 g) and 4-vinylquinoline (440 mg, 1 eq.) in wet dimethylformamide (15 mL). The reaction mixture was heated at 100° C. overnight. Further palladium diacetate (35 mg), triphenylphosphine (88 mg) and tetra-N-butylammonium chloride (0.8 g) were added and the reaction mixture heated at 130° C. for 60 hours. The reaction was diluted with water and extracted with dichloromethane. The organic extract was dried over sodium sulfate, filtered and concentrated under reduced pressure. The residue was purified via flash column chromatography, using a gradient of 10→16% ethyl acetate: petroleum ether as eluent, to give Intermediate (8) (368 mg, 26%). $^1$H NMR (CDCl$_3$) δ 8.69 (d, 1H, ArH); 6.67 (m, 1H, ArH); 6.58 (m, 1H, ArH); 0.69 (t, 3H, CH$_2$CH$_3$). TLC (silica gel): Rf=0.55 (30% ethyl acetate:petroleum ether).

Example 9

Preparation of Intermediate (9)

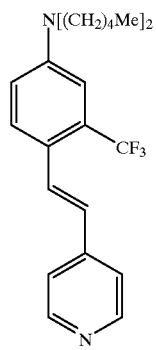

(9)

Palladium diacetate (6 mg, ca. 5 mol %) and tri-o-tolylphosphine (15 mg, ca. 10 mol %) were added to a solution of N,N-dipentyl-3-trifluoromethyl-4-bromoaniline (Intermediate 3) (190 mg, 0.5 mmol) and 4-vinylpyridine (0.15 mL, 3 eq.) in triethylamine (3 mL) in a reactivial. The reaction was heated at 110° C. for 5 days. The residue was purified via flash column chromatography, using a gradient of 20→27.5% ethyl acetate:petroleum ether as eluent, to give Intermediate (9) (27 mg). $^1$H NMR (CDCl$_3$) δ 8.52 (d, 2H, ArH); 7.68 (d, 1H, ArH); 7.33 (d, 2H, ArH); 3.32 (t, 4H, 2×NCH$_2$); 0.93 (t, 6H, 2×CH$_2$CH$_3$). TLC (silica): Rf=0.70 (50% ethyl acetate:petroleum ether).

Example 10

Preparation of Quinolinium, 4-[2-[4-(dipentylamino)-32-methyl-phenyl]ethenyl]-1-(sulfobutyl)-inner salt (10)

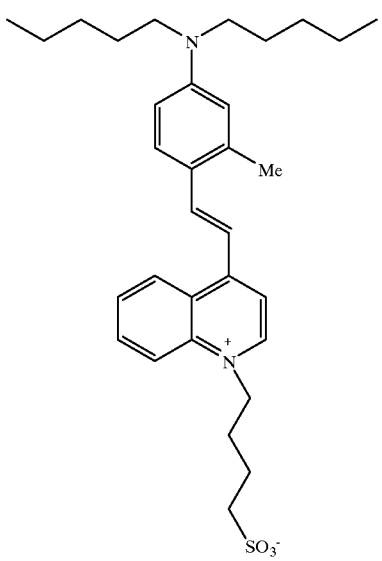

(10)

A mixture of Intermediate (5) (58 mg) and 1,4-butanesulfone (2 mL) was heated at 135° C. for 1 hour. The reaction mixture was diluted with dichloromethane (3 mL), loaded onto a column of silica and eluted with 1:1 ethyl acetate:ethanol to give quinolinium, 4-[2-[4-(dipentylamino)-3-methyl-phenyl]ethenyl]-1-(sulfobutyl)-, inner salt (10) (52 mg). $^1$H NMR (CDCl$_3$) δ 9.55 (d, 1H, ArH); 5.01 (t, 3H, N+CH$_2$); 0.78 (t, 6H, 2×CH$_3$). MS 537 (M+H).

Example 11

Preparation of Quinolinium, 4-[2-[4-(dipentylamino)-32-chloro-phenyl]ethenyl]-1-(sulfobutyl)-, inner salt (11)

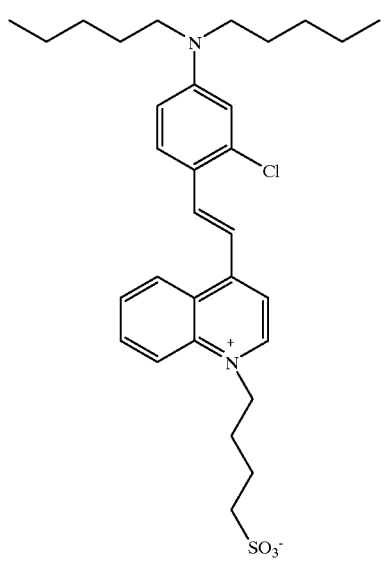

(11)

A mixture of Intermediate (6) (100 mg, 0.25 mmol) and 1,4-butanesultone (2 mL) was heated at 135° C. for 1 hour. The reaction mixture was diluted with dichloromethane (3 mL), loaded onto a column of silica and eluted with 1:1 ethyl acetate:ethanol to give quinolinium, 4-[2-[4-(dipentylamino)-3-chloro-phenyl]ethenyl]-1-(sulfobutyl)-, inner salt (11) (194mg). $^1$H NMR (CDCl$_3$) δ 9.75 (d, 1H, ArH); 5.03 (t, 3H, N(quat)CH$_2$); 0.77 (t, 6H, 2×CH$_3$). TLC (silica gel):Rf=0.34 (15% MeOH/dichloromethane)

Example 12

Preparation of Quinolinium, 4-[2-[4-(dipentylamino)-32-trifluoromethyl-phenyl]-thenyl]-1-(sulfobutyl)-, inner salt (12)

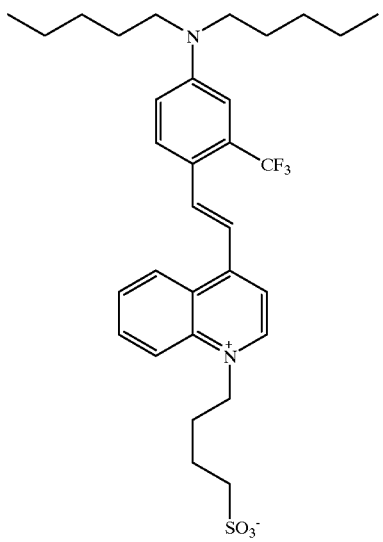

(12)

A mixture of Intermediate (7) (232 mg) and 1,4-butanesultone (2mL) were heated at 135° C. for 1 hour. The reaction mixture was diluted with dichloromethane (6 mL), loaded onto a column of silica and eluted using a gradient of 7:1→3:1 dichloromethane:methanol to give quinolinium, 4-[2-[4-(dipentylamino)-3-trifluoromethyl-phenyl]ethenyl]-1-(sulfobutyl)-, inner salt (12) (324 mg, 64%). $^1$H NMR (CD$_3$OD) δ 9.08 (d, 1H, ArH); 8.85 (dd, 1H, ArH); 4.96 (t, 2H, N$^+$CH$_2$); 0.93 (t, 6H, 2×CH$_3$). MS 613 (M+Na)$^+$; 591 (M+H).

Example 13

Preparation of Quinolinium, 4-[2-[4-(decylamino)-32-trifluoromethyl-phenyl]ethenyl]-1-(sulfobutyl)-, inner salt (13)

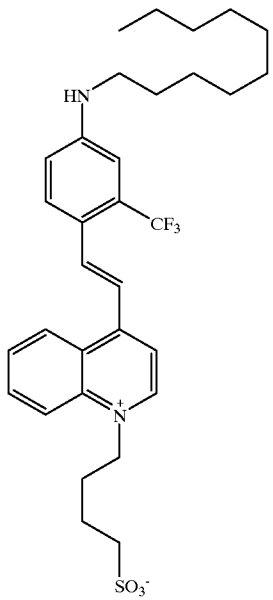

(13)

A mixture of Intermediate (8) (368 mg) and 1,4-butanesultone (3.5mL) were heated at 135° C. for 1 hour. The reaction mixture was diluted with dichloromethane (15mL), loaded onto a column of silica and eluted using a gradient of 9:1→3.5:1 dichloromethane:methanol to give quinolinium, 4-[2-[4-(decylamino)-3-trifluoromethyl-phenyl]ethenyl]-1-(sulfobutyl)-, inner salt (13) (344 mg). $^1$H NMR (CD$_3$OD+CDCl$_3$) δ 9.06 (d, 1H, ArH); 8.83 (m, 1H, ArH); 4.97 (t, 2H, N$^+$CH$_2$); 0.86 (t, 3H, CH$_3$). MS 613 (M+Na)$^+$; 591 (M+H)$^+$.

Example 14

Preparation of Pyridinium, 4-[2-[4-(dipentylamino)-32-trifluoromethyl-phenyl]ethenyl]-1-(sulfobutyl)-, inner salt (14)

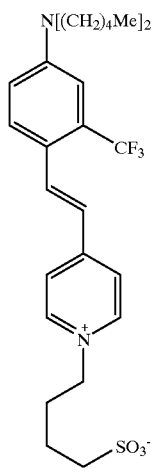

(14)

A mixture of Intermediate (9) (27 mg) and 1,4-butanesulfone (0.5 mL) were heated at 130° C. for 1 h. The reaction mixture was diluted with dichloromethane (3 mL), loaded onto a column of silica and eluted using a gradient of 7:1→3:1 dichloromethane:methanol to give pyridinium, 4-[2-[4-(dipentylamino)-3-trifluoromethyl-phenyl]ethenyl]-1-(sulfobutyl)-, inner salt (14) (24 mg). $^1$H NMR (CDCl$_3$) δ 8.64 (d, 2H, ArH); 7.94 (m, 2H, ArH); 4.48 (t, 2H, N$^+$CH$_2$); 3.40 (t, 4H, 2×NCH$_2$); 0.92 (t, 6H, 2×CH$_3$). MS 540 (M)$^+$. TLC (silica gel):Rf=0.1 (1:9 methanol:dichloromethane).

Example 15

Preparation of Intermediate (15)

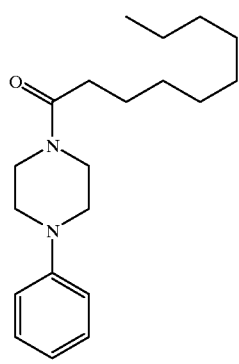

(15)

To a solution of N-phenylpiperazine (0.76 mL, 5 mmol) and N,N-diisopropylethylamine (1.74 mL, 2 eq.) in 10 ml of dry dichloromethane at 0° C., decanoyl chloride (1.25 mL, 1.2 eq.) was added dropwise. After 0.5 h the reaction mixture was partitioned between water and ether. The ether fraction was washed with aq. saturated NaHCO$_3$, dried over sodium sulfate and concentrated under reduced pressure to a yellow solid. This material was dissolved in a mixture of diethyl ether and petroleum ether and concentrated under reduced pressure until a white solid formed in solution. The white crystals were filtered off and washed with petroleum ether to give Intermediate (15) (780 mg, 50%). $^1$H NMR (CDCl$_3$)δ 7.26 (m, 3H, ArH); 6.97 (m, 2H, ArH); 3.20 (m, 4H, 2×NCH2); 0.81 (t, 3H, CH$_2$CH$_3$). TLC (silica gel): Rf=0.45 (40% ethyl acetate:petroleum ether).

Example 16

Preparation of Intermediate (16)

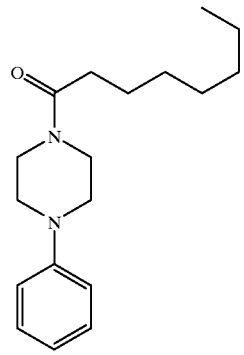

(16)

To a solution of N-phenylpiperazine (0.76 mL, 5 mmol) and N,N-diisopropylethylamine (1.74 mL, 2 eq.) in dry dichloromethane (10 mL) at 0° C., octanoyl chloride (1.02 mL, 1.2 eq.) was added dropwise. After 1h the reaction was quenched with aq. saturated NaHCO$_3$. After a further 15 min the resultant mixture was partitioned between water and ether. The ether fraction was washed with aq. saturated NaHCO$_3$, dried over sodium sulfate and concentrated under reduced pressure to ca. 10 mL. This concentrate was diluted with petroleum ether (200 mL) and cooled until white crystals formed. The crystals were filtered off and washed with petroleum ether to give Intermediate (16) (852 mg, 60%). TLC (silica gel): Rf=0.6 (60% ethyl acetate:petroleum ether).

Example 17
Preparation of Intermediate (17)

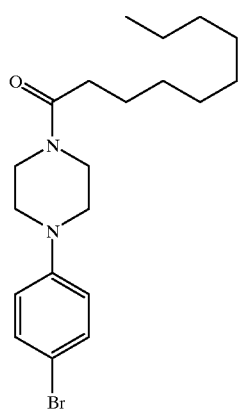

(17)

N-bromosuccinimide (440 mg, 1 eq.) was added to a solution of N-decanoyl-N'-phenylpiperazine (780 mg) in dimethylformamide (20 mL). After 1 h the reaction mixture was partitioned between water and dichloromethane. The organic fraction was washed with water, dried over sodium sulfate and concentrated under reduced pressure. The residue was purified via flash column chromatography using a gradient of 40→60% ethyl ether:petroleum ether as eluent to give Intermediate (17) (800 mg, 82%). $^1$H NMR δ(CDCl$_3$) δ 7.36 (d, 2H, ArH); 6.88 (d, 2H, ArH); 3.20 (m, 4H, 2×NCH$_2$); 0.65 (t, 3H, CH$_2$CH$_3$). TLC (silica gel) Rf0.45 (40% ethyl acetate:petroleum ether).

Example 18
Preparation of Intermediate (18)

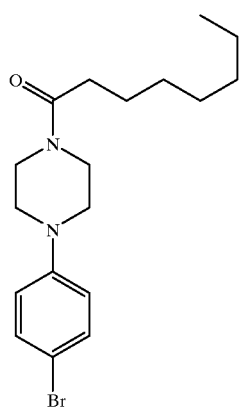

(18)

N-bromosuccinimide (526 mg, 1 eq.) was added to a solution of N-octanoyl-N'-phenylpiperazine (852 mg) in dimethylformamide (20 mL). After 3 h the reaction was partitioned between water and ethyl ether. The organic fraction was washed with water, dried over sodium sulfate and concentrated under reduced pressure. The residue was dissolved in ether (10 mL) and diluted with petroleum ether (200 mL) and then concentrated under reduced pressure until white crystals were deposited. The white crystals were filtered off and washed with petroleum ether to give Intermediate (18) (770 mg, 71%). $^1$H NMR (CDCl$_3$)δ 7.33 (d, 2H, ArH); 6.87 (m, 2H, ArH); 3.18 (m, 4H,2×NCH$_2$); 0.87 (t, 3H, CH$_2$CH$_3$). TLC (silica gel): Rf=0.6 (60% ethyl acetate:petroleum ether).

Example 19
Preparation of Intermediate (19)

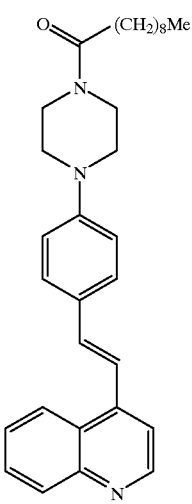

(19)

Palladium diacetate (7 mg, ca. 5 mol %), triphenylphosphine (17 mg, ca. 10 mol %), potassium acetate (180 mg, 2 eq.) and tetra-N-butylammonium chloride (210 mg, leq.) were added to a solution of Intermediate (17) (259 mg, 0.65 mmol) and 4-vinylquinoline (101 mg, 1 eq.) in dimethylformamide (4 mL). The reaction mixture was heated at 105° C. overnight. The reaction was then diluted with water and extracted with dichloromethane. The organic extract was dried over sodium sulfate, filtered and concentrated under reduced pressure. The residue was purified via flash column chromatography, using a gradient of 40→70% ethyl acetate:petroleum ether as eluent, to give Intermediate (19). $^1$H NMR (CDCl$_3$) δ 8.81 (d, 1H, ArH); 8.23 (t, 2H, ArH); 6.92 (d, 2H, ArH); 3.24 (m, 4H, 2×NCH$_2$); 0.84 (t, 3H,CH$_2$CH$_3$). TLC (silica gel): Rf=0.20 (60% ethyl acetate:petroleum ether).

Example 20
Preparation of Intermediate (20)

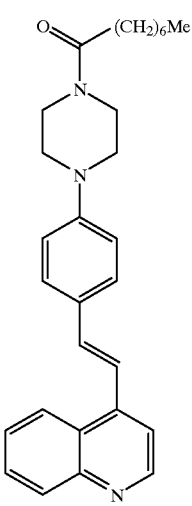

(20)

Palladium diacetate (11 mg, ca. 5 mol %) and triphenylphosphine (30 mg, ca. 10 mol %) were added to a solution of Intermediate (18) (367 mg, 1 mmol) and 4-vinylquinoline (155 mg, 1 eq.) in triethylamine (4 mL) in a reacti-vial. The reaction was heated to 110° C. for 48 hours. The reaction was then concentrated under reduced pressure. The residue was purified via flash column chromatography, using a gradient of 40→90% ethyl acetate-:petroleum ether as eluent, to give Intermediate (20) (160 mg, 36%). $^1$H NMR (CDCl$_3$) δ 8.89 (d, 1H, ArH); 8.26 (dd, 2H, ArH); 6.98 (d, 2H, ArH); 3.32 (m, 4H, 2×NCH$_2$); 0.92 (t, 3H, CH2CH$_3$).TLC (silica gel): Rf=0.20 (60% ethyl acetate:petroleum ether.)

Example 21

Preparation of Intermediate (21)

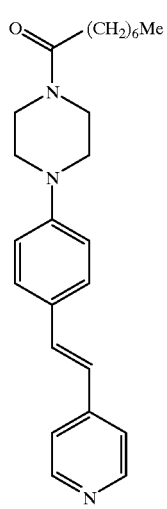

(21)

Palladium diacetate (6 mg, ca. 5 mol %) and triphenylphosphine (17 mg, ca. 10 mol %) were added to a solution of Intermediate (18) (200 mg, 0.54 mmol) and 4-vinylpyridine (0.12 mL, 2 eq.) in triethylamine (3 mL) in a reacti-vial. The reaction mixture was heated at 110° C. for 4 days. On cooling, the triethylamine solution was transferred from a solid precipitate and concentrated under reduced pressure. The residue was purified via flash column chromatography, using a gradient of 30→100% ethyl acetate:petroleum ether as eluent, to give Intermediate (21) (52 mg). $^1$H NMR (CDCl$_3$)δ 8.52 (d, 2H, ArH); 7.43 (d, 2H, ArH); 6.88 (d, 2H, ArH); 3.22 (m, 4H, 2×NCH$_2$); 0.84 (t, 3H, CH$_2$CH$_3$). TLC (silica gel): Rf=0.10 (60% ethyl acetate-:petroleum ether).

Example 22
Preparation of Intermediate (22)

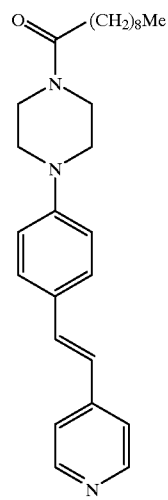

(22)

Palladium diacetate (8 mg, ca. 5 mol %) and tri-o-tolylphosphine (21 mg, ca. 10 mol %) were added to a solution of Intermediate (17) (270 mg, 0.68 mmol) and 4-vinylpyridine (0.15 mL, 2 eq.) in triethylamine (4 mL) in a reacti-vial. The reaction was heated at 110° C. for 4days. The reaction was cooled and concentrated under reduced pressure. The residue was purified via flash column chromatography, using a gradient of 40→100% ethyl acetate:petroleum ether as eluent, to give Intermediate (22) (130 mg). $^1$H NMR (CDCl$_3$)δ 8.52 (d, 2H, ArH); 7.45 (d, 2H, ArH); 6.89 (d, 2H, ArH); 3.22 (m, 4H, 2×NCH$_2$); 0.82 (t, 3H, CH$_2$CH$_3$). TLC (silica gel):Rf=0. 10 (60% ethyl acetate:petroleum ether).

Example 23
Preparation of Intermediate (23)

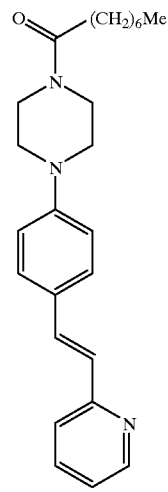

(23)

Palladium diacetate (6 mg, ca. 5 mol %) and tri-o-tolylphosphine (17 mg, ca. 10 mol %) were added to a solution of Intermediate (18) (200 mg, 0.54 mmol) and 2-vinylpyridine (0.18mL, 3 eq.) in triethylamine (3 mL) in a reacti-vial. The reaction was heated at 110° C. for 2days. The reaction was cooled, diluted with toluene and filtered to remove a white precipitate. The resultant solution was concentrated under reduced pressure and the residue was purified via flash column chromatography, using a gradient of 30→75% ethyl acetate:petroleum ether as eluent, to give Intermediate (23) (73 mg). $^1$H NMR (CDCl$_3$)δ 8.68 (d, 2H, ArH); 7.45 (d, 2H, ArH); 6.90 (d, 2H, ArH); 3.22 (m, 4H, 2×NCH$_2$); 0.88 (t, 3H, CH$_2$CH$_3$). TLC (silica gel):Rf=0.10 (50% ethyl acetate:petroleum ether).

Example 24
Preparation of Intermediate (24)

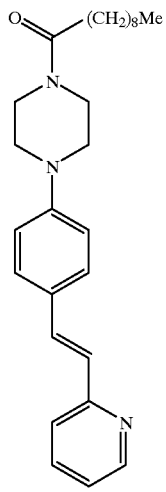

(24)

Palladium diacetate (6 mg, ca. 5 mol %) and tri-o-tolylphosphine (17 mg, ca. 1 mol %) were added to a solution of Intermediate (17) (200 mg, 0.5 mmol) and 2-vinylpyridine (0.15 mL, 3 eq.) in triethylamine (3 mL) in a reacti-vial. The reaction was heated at 110° C. for 2days. The reaction was cooled, diluted with toluene and filtered to remove a white precipitate. The resultant solution was concentrated under reduced pressure and the residue was purified via flash column chromatography, using a gradient of 40→70% ethyl acetate:petroleum ether as eluent, to give Intermediate (24) (138 mg). $^1$H NMR (CDCl$_3$)δ 8.57 (d, 2H, ArH); 7.34 (d, 2H, ArH); 6.90 (d, 2H, ArH); 3.22 (m, 4H, 2×NCH$_2$); 0.88 (t, 3H, CH$_2$CH$_3$). TLC (silica gel):Rf=0.10 (50% ethyl acetate:petroleum ether).

Example 25
Preparation of Quinolinium, 4-[2-[4-[(1-oxodecyl)piperazinyl]phenyl]ethenyl]1-(sulfobutyl)-, inner salt (25)

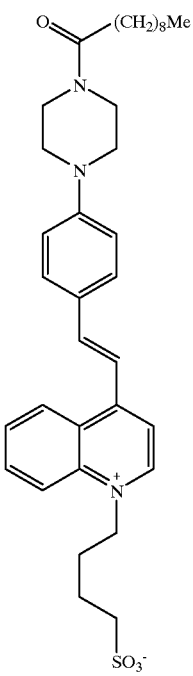

(25)

A mixture of the total product of Intermediate (19) and 1,4-butanesultone (2 mL) were heated at 135° C. for 1.5 h. The reaction mixture was diluted with dichloromethane (6 mL), loaded onto a column of silica and eluted using a gradient of 7:1→3:1 dichloromethane:methanol to give quinolinium, 4-[2-[4-[(1-oxodecyl)piperazinyl]-phenyl]ethenyl]-1-(sulfobutyl)-, inner salt (25) (70 mg). $^1$H NMR (CD$_3$OD)δ 8.98 (d, 1H, ArH); 8.81 (m, 1H, ArH); 3.73 (t, 4H, 2×NCH$_2$); 0.84 (t, 3H, CH$_3$).MS 605 (M$^+$)

Example 26
Preparation of Quinolinium, 4-[2-[4-[(1-oxooctyl)piperazinyl]phenyl]ethenyl]1-(sulfobutyl)-, inner salt (26)

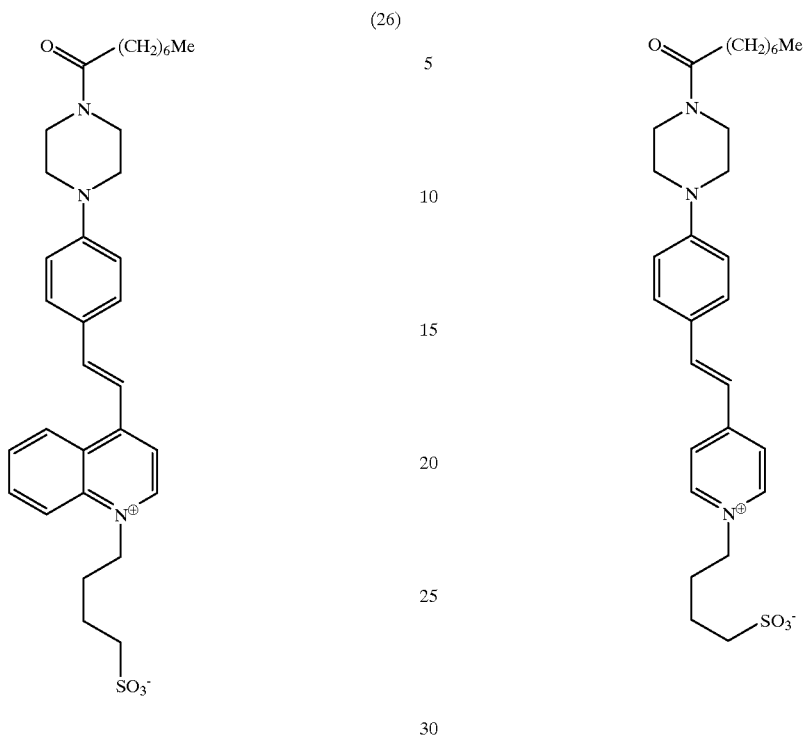

A mixture of Intermediate (20) (160 mg) and 1,4-butanesultone (2.5 mL) were heated at 130° C. for 1 h. The reaction mixture was diluted with dichloromethane (8 mL), loaded onto a column of silica and eluted using a gradient of 7:1→2.5:1 to give dichloromethane:methanol quinolinium, 4-[2-[4-[(1-oxooctyl)-piperazinyl]phenyl]ethenyl]-1-(sulfobutyl)-, inner salt (26) (176 mg). $^1$H NMR (CD$_3$OD+CD$_3$COCD$_3$) δ 9.09 (d, 1H, ArH); 8.90 (m, 1H, ArH); 5.02 (t, 2H, N+CH$_2$); 3.75 (t,4H, 2×NCH$_2$); 0.88 (t, 3H, CH$_3$). TLC (silica gel): Rf=0.10 (10% methanol: dichloromethane).

Example 27
Preparation of Pyridinium, 4-[2-[4-[(1-oxooctyl) piperazinyl]phenyl]ethenyl]-(sulfobutyl)-, inner salt (27)

A mixture of Intermediate (21) (47 mg) and 1,4-butanesultone (1 mL) were heated at 130° C. for 1 h. The reaction mixture was diluted with dichloromethane (5 mL), loaded onto a column of silica and eluted using a gradient of 7:1→2:1 dichloromethane:methanol to give pyridinium, 4-[2-[4-[(1-oxooctyl)piperazinyl]-phenyl]ethenyl]-1-(sulfobutyl)-, inner salt (27) (45 mg). $^1$H NMR (CD$_3$OD) δ 8.67 (d, 2H, ArH); 8.04 (d, 2H, ArH); 4.53 (t, 2H, N$^+$CH$_2$); 3.72 (m, 4H, 2×NCH$_2$); 0.92 (m, 3H, CH$_3$).). MS 527 (M)$^+$. TLC (silica gel): Rf=0.05 (1:7 methanol: dichloromethane).

Example 28
Preparation of Pyridinium, 4-[2-[4-[(1-oxodecyl) piperazinyl]phenyl]ethenyl]1-(sulfobutyl)-, inner salt (28)

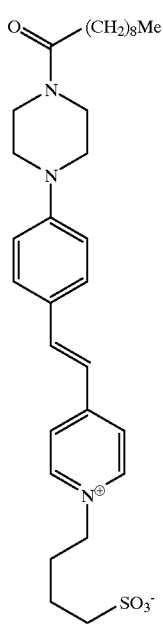

(28)

A mixture of Intermediate (22) (127 mg) and 1,4-butanesultone (2mL) were heated at 130° C. for 1 h. The reaction mixture was diluted with dichloromethane (8 mL), loaded onto a column of silica and eluted using a gradient of 7:1→2:1 dichloromethane:methanol to give pyridinium, 4-[2-[4-[(1-oxooctyl)piperazinyl]-phenyl]ethenyl]-1-(sulfobutyl)-, inner salt (28) (162 mg). $^1$H NMR (CDCL$_3$) δ 8.63 (d, 2H, ArH); 7.98 (d, 2H, ArH); 4.48 (t, 2H, N$^+$CH$_2$); 3.73 (m, 4H, 2×NCH$_2$); 0.87 (m, 3H, CH$_3$).). MS 555 (M)$^+$. TLC (silica gel): Rf=0.05 (1:7 methanol: dichloromethane).

Example 29
Preparation of Pyridinium, 2-[2-[4-[(1-oxooctyl)piperazinyl]phenyl]ethenyl]1-(sulfobutyl)-, inner salt (29)

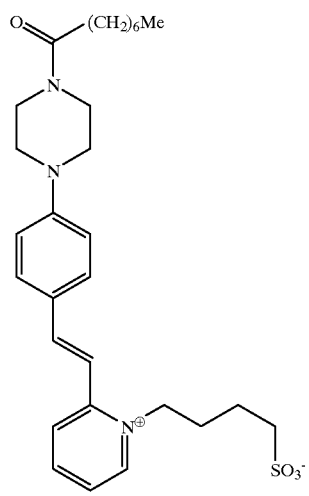

(29)

A mixture of Intermediate (23) (70 mg) and 1,4-butanesultone (1 mL) were heated at 130° C. for 1 h. The reaction mixture was diluted with dichloromethane (8 mL), loaded onto a column of silica and eluted using a gradient of 7:1→3:1 dichloromethane:methanol to give pyridinium, 4-[2-[4-[(1-oxooctyl)piperazinyl]-phenyl]ethenyl]-1-(sulfobutyl)-, inner salt (29) (41 mg). $^1$H NMR (CDCL$_3$) δ 8.72 (d, 1H, ArH); 7.03 (d, 2H, ArH); 4.73 (t, 2H, N$^+$CH$_2$); 3.73 (m, 4H, 2×NCH$_2$); 0.88 (m, 3H, CH$_3$).). MS 526 (M−H)$^+$.

Example 30
Preparation of Pyridinium, 2-[2-[4-[1(1-oxodecyl)piperazinyl]phenyl]ethenyl] 1-(sulfobutyl)-, inner salt (30)

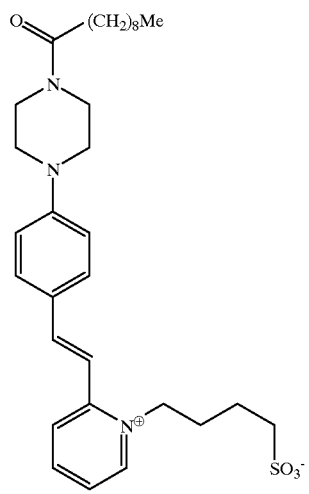

(30)

A mixture of Intermediate (24) (133 mg) and 1,4-butanesultone (1.5 mL) were heated at 130° C. for 1 h. The reaction mixture was diluted with dichloromethane (6 mL), loaded onto a column of silica and eluted using a gradient of 7:1→3:1 dichloromethane:methanol to give pyridinium, 2-[2-[4-[(1-oxooctyl)piperazinyl]-phenyl]ethenyl]-1-(sulfobutyl)-, inner salt (30) (110 mg). $^1$H NMR (CDCL$_3$) δ 8.72 (d, 1H, ArH); 7.02 (d, 2H, ArH); 4.73 (t, 2H, +CH$_2$); 3.72 (m, 4H, 2×NCH$_2$); 0.87 (m, 3H, CH$_3$).). MS 554 (M−H)$^+$. TLC (silica gel): Rf=0.05 (1:9 methanol: dichloromethane).

Example 31
Preparation of Intermediate (31)

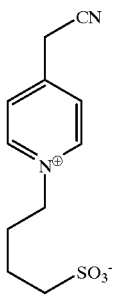

(31)

4-Acetonitrilepyridine hydrochloride (465 mg, 3 mmol) was dissolved in 4 ml of water and neutralized with solid K$_2$CO$_3$ (205 mg). The solution was partitioned between water and ethyl acetate and the organic layer washed with water, dried and concentrated to a solid. The solid was dissolved in a 2 ml of 1,4-butanesultone and stirred at 110° C. for 2 h. The reaction mixture was diluted with acetone and solid precipitated. The mixture was stirred for 15 mins to grind up the purple solid then filtered. The solid was washed with acetone and dried to give Intermediate (31) (514 mg, 67%). $^1$H NMR (d$^6$-DMSO) δ 9.24 (d,2H, ArH); 8.27 (d, 2H, ArH); 4.77 (t, 2H, N$^+$CH$_2$). TLC (silica gel): Rf=0.45 (1:1 dichloromethane:methanol).

Example 32
Preparation of N,N-Dihexyl-4-aminobenzaldehyde (32).

To a solution of dry DMF (1.1. mL) under Argon at 0° C. was added of POC13(375 μL, 4 mmol). N,N-Dihexylaniline (1.04 g, 4 mmol) was added dropwise and the solution was mixed with rapid stirring to form a green solution. The reaction mixture was heated at 95° C. for 2 h. The solution quickly turned red/brown. After 2 h the solution was cooled. It was poured into ice/water 20 mL and aq. saturated NaOAc (20 mL) was added. The partially neutralized solution was partitioned between ether and water. The ether layer was washed with aq. saturated NaHCO3 and dried over sodium sulfate. After concentrating to approximately 20 mL. DMF oiled out of the solution. The solution was transferred from the oil and concentrated under reduced pressure. The resultant residue was purified via flash column chromatography, using a gradient of 0→20% ethyl acetate; petroleum ether as eluent to give N,N-Dihexyl-4-aminobenzaldehyde (32) (970 mg, 84%). $^1$H NMR (CDCl$_3$) δ 9.72 (s, 1H CHO); 7.70 (d, 2H, ArH); 6.64 (d, 2H, ArH); 3.32 (t, 4H, 2×NCH$_2$); 0.89 (t, 6H 2×CH$_2$CH$_3$). TLC (silica gel): Rf=0.75 (20% ethyl acetate;petroleum ether).

Example 33
Preparation of Pyridinium, 4-[2-[4-(dibutylamino)phenyl]-1-cyano-ethenyl]-1-(sulfobutyl)-, inner salt (33)

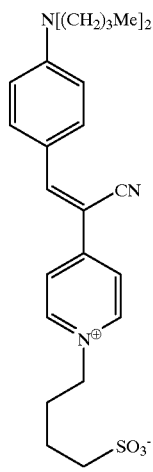

(33)

N,N-Dibutyl-4-aminobenzaldehyde (96 mg, 0.41 mmol) was dissolved in ethanol (1.5 ml) and Intermediate (31) (125 mg, 1.2 eq) was added. A red colour began to form. Pyrrolidine (50 μL) was added to the solution and the solid sultone immediately dissolved. After stirring overnight a red solid had formed and was collected by filtration and dried to give pyridinium, 4-[2-[4-(dibutylamino)phenyl]-1-cyano-ethenyl]-1-(sulfobutyl-, inner salt (33) (161 mg, 84%). $^1$H NMR (d$^6$-DMSO) δ 8.72 (d, 2H, ArH); 6.83 (d, 2H, ArH); 4.54 (t, 2H N$^+$CH$_2$); 0.93 (t, 6H, 2×CH$_2$CH$_3$). TLC (silica gel): Rf=0.2 (7:1dichloromethane:methanol)

Example 34
Preparation of Pyridinium, 4-[2-[4-(dihexylamino)phenyl]-1-cyano-ethenyl]-1-(sulfobutyl)-, inner salt (34)

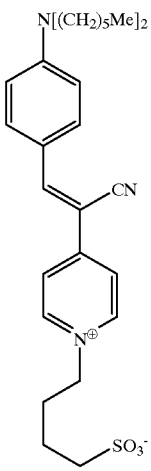

(34)

To a solution of Intermediate (32) (159 mg, 1.1. eg.) in ethanol (2 mL) was added Intermediate (31) (127 mg, 0.5 mmol). A red colour began to form in the purple suspension. Pyrrolidine (50 μL) was added and the suspension dissolved to give a dark red solution. After 7 h, a heavy red precipitate had formed in the flask. This was filtered off; washed with ethanol and diethyl ether and dried to give pyridinium, 4-[2-[4-(dihexylamino)phenyl]-1-cyano-ethenyl]-1-(sulfobutyl), inner salt (34) (176 mg, 67%). $^1$HMR (CD$_3$OD+D$_2$O) δ 8.73 (d, 2H, ArH); 6.89 (d, 2H, ArH); 4.59 (t, 2H, N$^+$CH$_2$); 0.94 (t, 6H 2×CH$_2$CH$_3$). MS 527 (M+H)$^+$.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

All references disclosed herein are hereby incorporated by reference in their entirety.

What is claimed is:
1. A compound of formula I

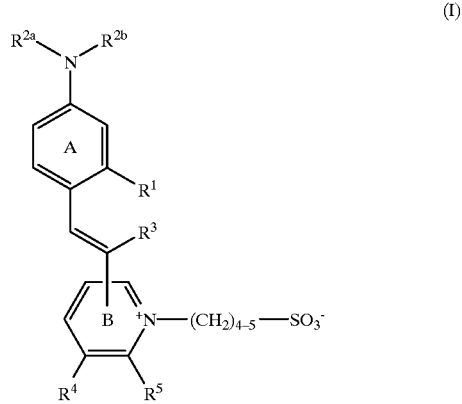

(I)

wherein
R$^1$ is (C$_1$–C$_6$) straight or branched chain alkyl, halogen or —CF$_3$;
either R$^{2a}$ and R$^{2b}$ are independently (C$_1$–C$_{20}$) straight or branched chain alkyl, (C$_1$–C$_{20}$) straight or branched chain aralkyl or H, $R^{2a}$ and $R^{2b}$ not simultaneously being H, or $R^2a$ and $R^2b$ are taken together and form a morpholinyl, piperidinyl or pyrrolidinyl ring;

$R^3$ is H or $(C_1-C_6)$ straight or branched chain alkyl; and either $R^4$ and $R^5$ are both H, or $R^4$ and $R^5$ taken together are —CH=CH—CH=CH—, the aromatic rings A and B, the —$(CH_2)_{4-5}$— group, and the —C(H)=C($R^3$)— group being optionally substituted with one or more —OH, $(C_1-C_6)$ straight or branched chain alkoxyl, halogen, $(C_1-C_6)$ straight or branched chain haloalkyl, pyridyl, thiophenyl, furyl, and phenyl, the phenyl being optionally substituted with one or more —OH, $(C_1-C_6)$ straight or branched chain alkyl or $(C_1-C_6)$ straight or branched chain alkoxyl.

2. The compound of claim 1, selected from the group consisting of:

Quinolinium, 4-[2-[4-(dipentylamino)-32-chlorophenyl]ethenyl]-1-(sulfobutyl)-, inner salt;

Quinolinium, 4-[2-[4-(dipentylamino)-32-trifluoromethylphenyl]ethenyl]-1-(sulfobutyl)-, inner salt;

Quinolinium, 4-[2-[4-(dipentylamino)-32-methylphenyl]ethenyl]-1-(sulfobutyl)-, inner salt;

Quinolinium, 4-[2-[4-(decylamino)-32-trifluoromethylphenyl]ethenyl]-1-(sulfobutyl)-, inner salt; and Pyridinium, 4-[2-[4-(dipentylamino)-32-trifluoromethylphenyl]ethenyl]-1-(sulfobutyl)-, inner salt.

3. The compound of claim 1, selected from the group consisting of:

Quinolinium, 4-[2-[4-(dipentylamino)-32-trifluoromethylphenyl]ethenyl]-1(sulfobutyl)-, inner salt;

Quinolinium, 4-[2-[4-(dipentylamino)-32-chlorophenyl]ethenyl]-1-(sulfobutyl)-, inner salt;

Quinolinium, 4-[2-[4-(decylamino)-32-trifluoromethylphenyl]ethenyl]-1-(sulfobutyl)-, inner salt; and Pyridinium, 4-[2-[4-(dipentylamino)-32-trifluoromethylphenyl]ethenyl]-1-(sulfobutyl)-, inner salt.

4. A compound of formula I

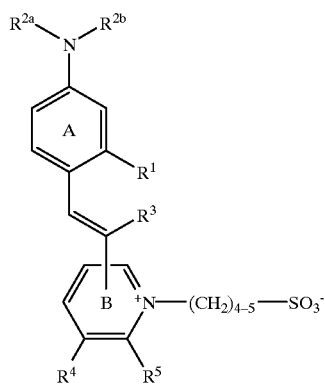

(I)

wherein $R^1$ is H, $(C_1-C_6)$ straight or branched chain alkyl, halogen or —$CF_3$;

$R^{2a}$ and $R^{2b}$ are taken together to form —$(CH_2)_2$—$NR^6$—$(CH_2)_2$—, wherein $R^6$ is $(C_1-C_{12})$ straight or branched chain alkyl, $(C_1-C_{12})$ straight or branched chain alkylcarbonyl or $(C_1-C_{12})$ straight or branched chain alkylsulphonyl;

$R^3$ is H; and either $R^4$ and $R^5$ are both H, or $R^4$ and $R^5$ are taken together and form —CH=CH—CH=CH—, the aromatic rings A and B, the —$(CH_2)_{4-5}$— group, and the —C(H)=C($R^3$)— group being optionally substituted with one or more —OH, $(C_1-C_6)$ straight or branched chain alkoxyl, halogen, $(C_1-C_6)$ straight or branched chain haloalkyl, pyridyl, thiophenyl, furyl, and phenyl, the phenyl being optionally substituted with one or more —OH, $(C_1-C_6)$ straight or branched chain alkyl or $(C_1-C_6)$ straight or branched chain alkoxyl.

5. The compound of claim 4, selected from the group consisting of:

Quinolinium, 4-[2-[4-[(1-oxooctyl)piperazinyl]phenyl]ethenyl]-1-(sulfobutyl)-, inner salt;

Quinolinium, 4-[2-[4-[(1-oxodecyl)piperazinyl]phenyl]ethenyl]-1-(sulfobutyl)-, inner salt;

Pyridinium, 4-[2-[4-[(1-oxooctyl)piperazinyl]phenyl]ethenyl]-1-(sulfobutyl)-, inner salt;

Pyridinium, 4-[2-[4-[(1-oxodecyl)piperazinyl]phenyl]ethenyl]-1-(sulfobutyl)-, inner salt;

Pyridinium, 2-[2-[4-[(1-oxooctyl)piperazinyl]phenyl]ethenyl]-1-(sulfobutyl)-, inner salt; and Pyridinium, 2-[2-[4-[(1-oxodecyl)piperazinyl]phenyl]ethenyl]-1-(sulfobutyl)-, inner salt.

6. A compound of formula I

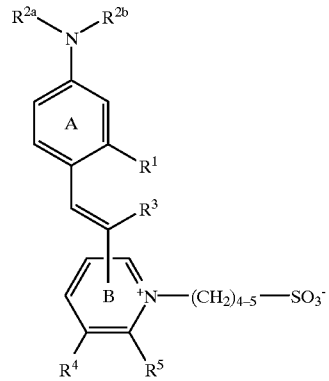

(I)

wherein $R^1$ is H, $(C_1-C_6)$ straight or branched chain alkyl, halogen, or —$CF_3$;

either $R^{2a}$ and $R^{2b}$ are independently $(C_1-C_{20})$ straight or branched chain alkyl, $(C_1-C_{20})$ straight or branched chain aralkyl or H, $R^{2a}$ and $R^{2b}$ not simultaneously being H, or $R^{2a}$ and $R^{2b}$ are taken together and form a morpholinyl, piperidinyl, pyrrolidinyl, or piperazinyl ring, wherein the piperazinyl ring is optionally substituted with $(C_1-C_{12})$ straight or branched chain alkyl, $(C_1-C_{12})$ straight or branched chain alkylcarbonyl or $(C_1-C_{12})$ straight or branched chain alkylsulphonyl;

$R^3$ is —CN, $CONH_2$, —COOH, or —COOR, wherein R is $(C_1-C_6)$ straight or branched chain alkyl or $(C_1-C_{10})$ straight or branched chain aralkyl, the —$CONH_2$ group being optionally substituted with one or two ($C_1$–$C_6$) alkyl groups or one or two ($C_1$–$C_{10}$) aralkyl groups; and either $R^4$ and $R^5$ are both H, or $R^4$ and $R^5$ are taken together and form —CH=CH—CH=CH—, the aromatic rings A and B, the —(CH$_2$)$_{4-5}$— group, and the —C(H)=C(R$^3$)— group being optionally substituted with one or more —OH, ($C_1$–$C_6$) straight or branched chain alkoxyl, halogen, ($C_1$–$C_6$) straight or branched chain haloalkyl, pyridyl, thiophenyl, furyl, and phenyl, the phenyl being optionally substituted with one or more —OH, ($C_1$–$C_6$) straight or branched chain alkyl, or ($C_1$–$C_6$) straight or branched chain alkoxyl.

7. The compound of claim 6, wherein $R^3$ is —CN.

8. The compound of claim 6, selected from the group consisting of:

Pyridinium, 4-[2-[4-(dibutylamino)phenyl]-1-cyanoethenyl]-1-(sulfobutyl)-, inner salt; and Pyridinium, 4-[2-[4-(dihexylamino)phenyl]-1-cyanoethenyl]-1-(sulfobutyl)-, inner salt.

* * * * *

UNITED STATES PATENT AND TRADEMARK OFFICE
CERTIFICATE OF CORRECTION

PATENT NO. : 6,335,446 B1
DATED : January 1, 2002
INVENTOR(S) : Pennnigton et al.

It is certified that error appears in the above-identified patent and that said Letters Patent is hereby corrected as shown below:

Column 29,
Lines 19, 21 and 24, replace "32" with -- 2 --;
Lines 26, 29 and 34, replace "32" with -- 2 --;
Line 38, replace "32" with -- 2 --;
Line 40, replace "32" with -- 2 --; and
Line 43, replace "32" with -- 2 --;

Signed and Sealed this

Sixth Day of August, 2002

Attest:

JAMES E. ROGAN
*Attesting Officer*   *Director of the United States Patent and Trademark Office*